United States Patent [19]

Fu et al.

[11] Patent Number: 5,817,319
[45] Date of Patent: Oct. 6, 1998

[54] FREE-FLOWING, NON-DUSTING WATER DISPERSIBLE GRANULES HAVING LOW FRIABILITY AND SUPERIOR CRUSH STRENGTH WHICH ARE CAPABLE OF FORMING STABLE SUSPENSIONS IN WATER WITHOUT DELETERIOUS FOAMING

[75] Inventors: Edward Fu, Newark, Del.; Ratan K. Chaudhuri, Butler; Kolazi S. Narayanan, Palisades Park, both of N.J.

[73] Assignee: ISP Investments Inc., Wilmington, Del.

[21] Appl. No.: 978,014

[22] Filed: Nov. 18, 1992

[51] Int. Cl.$^6$ ..................................................... A01N 25/14
[52] U.S. Cl. ........................ 424/407; 424/405; 424/409; 424/419
[58] Field of Search ............................ 526/264; 424/405, 424/408, 409, 489, 501, 407, 419

[56] References Cited

U.S. PATENT DOCUMENTS

| | | | |
|---|---|---|---|
| 2,667,473 | 1/1954 | Morner | 526/264 |
| 3,142,664 | 7/1964 | Bauer | 526/264 |
| 5,185,170 | 2/1993 | Kopolow | 526/264 |
| 5,230,892 | 7/1993 | Feyen et al. | 424/409 |
| 5,231,070 | 7/1993 | Narayanan et al. | 504/113 |

FOREIGN PATENT DOCUMENTS 3007202  1/1991  Japan.

Primary Examiner—Neil S. Levy
Attorney, Agent, or Firm—William J. Davis; Marilyn J. Maue; Walter Katz

[57] ABSTRACT

A free-flowing, non-dusting water dispersible granule of an active agricultural chemical having low friability and effective crush strength for delivery to a desired site as a stable suspension in water, without deleterious foaming, which granule includes about 1–25% by weight thereof of a binder which is a copolymer of (a) polyvinylpyrrolidone and (b) a comonomer selected from a $C_4$–$C_{30}$ alkene and vinyl acetate, and mixtures thereof.

7 Claims, 2 Drawing Sheets

FREE-FLOWING, NON-DUSTING WATER DISPERSIBLE GRANULES HAVING LOW FRIABILITY AND SUPERIOR CRUSH STRENGTH WHICH ARE CAPABLE OF FORMING STABLE SUSPENSIONS IN WATER WITHOUT DELETERIOUS FOAMING

BACKGROUND OF THE INVENTION

1. Field of the Invention

This invention relates to water dispersible granules (WDG) of active agricultural chemicals, and, more particularly, to free-flowing, non-dusting WDGs of such chemicals, which are characterized by low granule friability and superior granule crush strength, and which granules will form stable suspensions in water, without deleterious foaming; for effective delivery and application of such chemicals at a desired site.

2. Description of the Prior Art

WDGs are important delivery vehicles for active agricultural chemicals because they are organic solvent-free, unlike emulsion concentrates, do not have dusting problems present with wettable powders, and can be transported more economically than suspension concentrates. WDGs are prepared by water-bonding particles of the active component. However, in the absence of a binder additive in the system, the granules will gradually lose cohesiveness as the water content is reduced by evaporation. An effective binder additive, therefore, must provide for effective granular crush strength and low friability, while enabling the granules to form stable suspensions in water during use, without deleterious foaming as a result thereof, and to quickly dissipate its binding action when immersed in water.

Ligninsulfonate has been considered the binder of choice in WDG systems. Polyvinylpyrrolidone, in combination with urea, has been suggested for the same use (Canadian Patent 1,209,363). However, there is a need for new and improved WDG systems in which the binder additive will provide free-flowing, non-dusting granules have low granule friability and superior crush strength, and which granules will form stable suspensions in water, without deleterious foaming, for effective delivery and application of such chemicals at a desired site.

IN THE DRAWINGS

FIGS. 1 and 2 are graphs of crush strength vs. granulation moisture for the granules of the invention.

SUMMARY OF THE INVENTION

A free-flowing, non-dusting water dispersible granule of an active agricultural chemical having low friability and effective crush strength for delivery to a desired site as a stable suspension in water, without deleterious foaming, which granule includes about 1–25%, preferably 1–6%, and, most preferably, 2–3%, by weight thereof of a binder which preferably is a copolymer of (a) polyvinylpyrrolidone and (b) a comonomer selected from a $C_4$–$C_{30}$ alkene and vinyl acetate, and mixtures thereof.

DETAILED DESCRIPTION OF THE INVENTION

Figure 1:
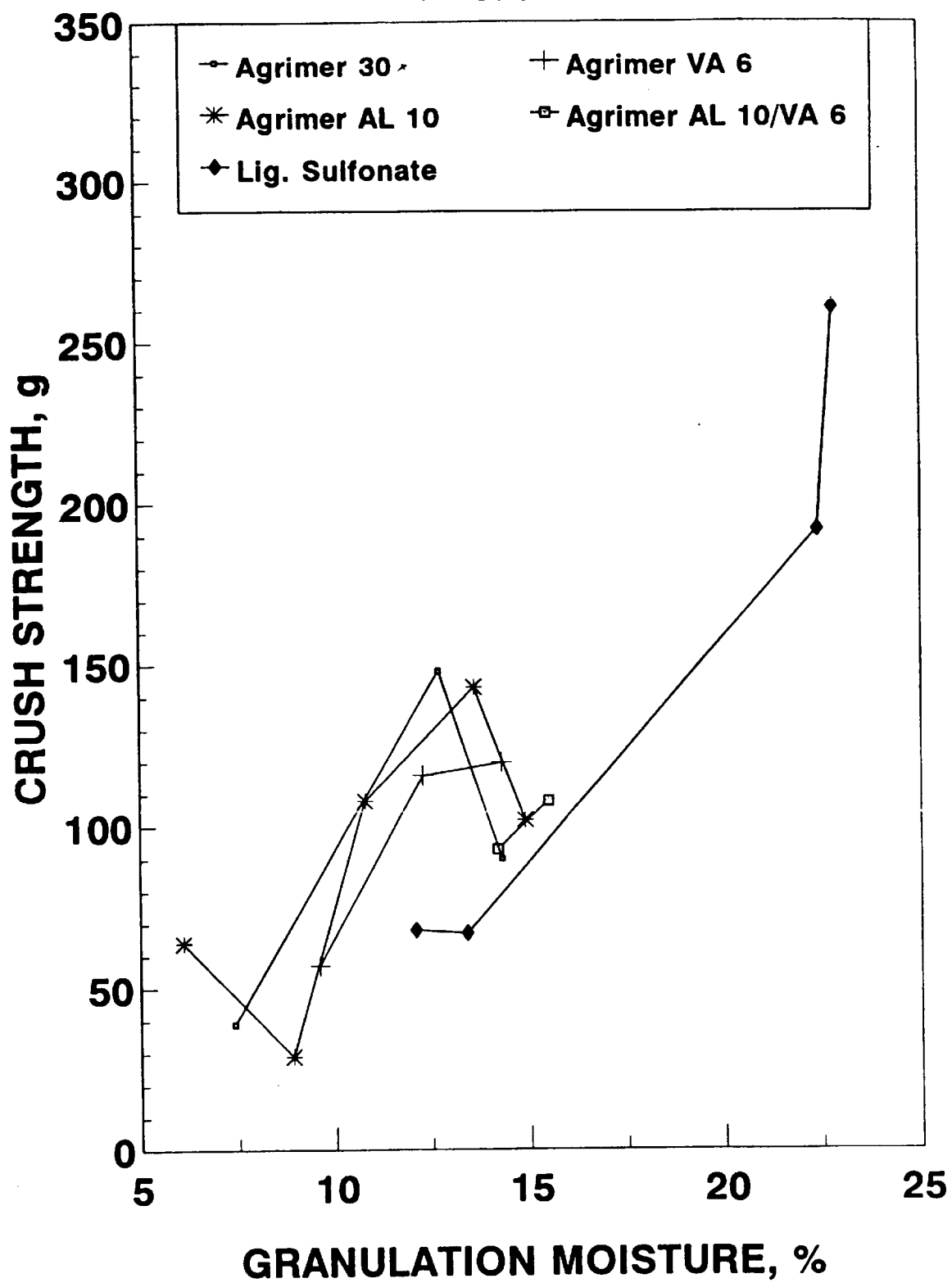

The binder component of the composition of the invention suitably is a copolymer of (a) a crosslinked or non-crosslinked N-alkenyl lactam homopolymer or copolymer in which the lactam unit of the polymer is represented by the formula

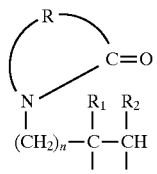

wherein R is $C_3$ to $C_6$ alkylene optionally substituted with $C_1$ to $C_{20}$ alkyl; $R_1$ and $R_2$ are each independently $C_2$ to $C_{20}$ alkyl or hydrogen and n has a value of from 0 or 2, and mixtures thereof, and (b) a $C_2$ to $C_{30}$ comonomer selected from the group of an alkenoic acid; an alkenyl-anhydride, ester, ether, amino ester or amino amide and an alpha mono- or di-olefin.

A preferred binder is a copolymer of (a) polyvinylpyrrolidone and (b) a comonomer selected from a $C_4$–$C_{30}$ alkene and vinyl acetate, and mixtures thereof.

Suitably, the binder is present in an amount of 1–25%, preferably 1–6%, and, most preferably, 2–3%.

1. WDG Formulation

A representative WDG formulation of the invention is given in Table 1 below.

TABLE 1

|  | % by Wt. |
|---|---|
| Atrazine | 92.3 |
| Binder Additive | 3.0 |
| Dispersant | 3.0 |
| Wetting agent | 1.5 |
| Defoamer | 0.2 |
|  | 100.0 |

2. Preparation of WDG (Granulation Procedure)

The weighed ingredients of the WDG/simulation (a total of 200 g to 1 kg) were mixed in a V-shell blender for 10 min. and transferred to a 24-inch pan granulator set at an angle of 50° and a speed of 13 r/min. Granulation was effected by spraying the ingredients with tap water. After granulation, the sample was dried in an oven at 40° C. for at least 6 hour to reduce the moisture level from 10–15% to under 1.5%. Finally, the sample was sieved to yield a free-flowing, non-dusting product having a particle size between 10 and 40 mesh (0.425 mm to 2.0 mm). The granules also can be made by extrusion followed by drying of the extruded product.

3. Test Procedures

Cone Dispersion—15 g. of sample was dispersed in 800 mL of 342 ppm hard water.(hardness equivalent to $CaCO_3$) by stirring with a magnetic stir bar for 2 min. The suspension was poured into a 1 L Imhoff dispersion cone, and allowed to settle for 5 min. The sediment volume was then determined, and a sedimentation index was calculated as follows $$Sed.\ Index = \frac{sed.\ vol.\ (mL)}{sample\ wt.\ (g)} \times 100$$

Crush Strength—Granules were sieved to provide a sample in the −10+12 mesh range. Granules were placed on balance and crushed firmly with a spatula. The force registered at breakage was recorded as the crush strength. The median of 15 to 20 measurements was reported.

Filtration Suspension—A quantity of sample containing 1 g of technical was added to 250 mL of 342 ppm hard water in a Fleaker™. After 5 min, the Fleaker™ was inverted 30 times to disperse the sample. Immediately, the suspension was then poured into an Imhoff dispersion cone. After 30 min, the upper 90% of the suspension was removed by aspiration. The remaining sample was vacuum filtered through a No. 3 Whatman filter paper, dried, and weighed to determine residual solids. The percent suspended was calculated as follows:

$$\% \; Susp. = \frac{[sample\; wt - (residual\; wt - 0.1 \times sample\; wt)]}{sample\; wt} \times 100$$

where the sample wt consists only of insoluble components of the formulation.

Friability—Measurements were carried out on a Vanderkamp® friabilator. 10 g of sample, initially between 10 and 40 mesh in size, was loaded into a Roche drum. 25 PFTE balls of 0.6 cm diameter were also loaded into the drum, which was then attached to the friabilator. The sample was subjected to 400 rotations, where each rotation causes the sample to fall a distance of 15 cm. Afterwards, the sample was sieved through a 40 mesh screen, and the weight of sample remaining above 40 mesh was determined. A friability index was calculated as follows:

$$Friability\; Index = \frac{sample\; wt\; above\; 40\; mesh}{total\; sample\; wt} \times 100$$

Foaming—100 mL of 342 ppm hard water and 5 g of sample were added to a 500 mL fleaker. The suspension was shaken vigorously by hand 60 times, and then allowed to settle for 2 min. The suspension was again shaken 60 times, after which the foam height was measured after 10 s and 2 min. The last step was repeated to produce a second set of values at 10 s and 2 min. A foaming index was calculated as follows:

$$Foam\; Index^* = \frac{(10\; s\; ht \times 2\; min\; ht^{**})_1 + (10\; s\; ht \times 2\; min\; ht)_2}{20}$$

4. EXAMPLES

Example 1

Water dispersible granules were prepared with ligninsulfonate binder according to the typical formulation and procedures described previously. Results are plotted in FIGS. 1 and 2 and Tables 2 and 3.
* Foam Index as defined above is the average of two readings divided by 10.
** in millimeters

Example 2

Water dispersible granules were prepared with Agrimer® VA 6, a copolymer of vinyl pyrrolidone and vinyl acetate, as binder according to the typical formulation and procedures described previously. Results are plotted in FIGS. 1 and 2 and Tables 2 and 3.

Example 3

Water dispersible granules were prepared with Agrimer® AL 10, a polyvinylpyrrolidone grafted with butene, as binder according to the typical formulation and procedures described previously. Results are plotted in FIGS. 1 and 2 and Tables 2 and 3.

Example 4

Water dispersible granules were prepared with a 1:1 by weight mixture of Agrimer® VA 6 and Agrimer® AL 10 as binder according to the typical formulation and procedures described previously. Results are plotted in FIGS. 1 and 2 and Table 2.

5. Discussion of Test Results

Figure 2:
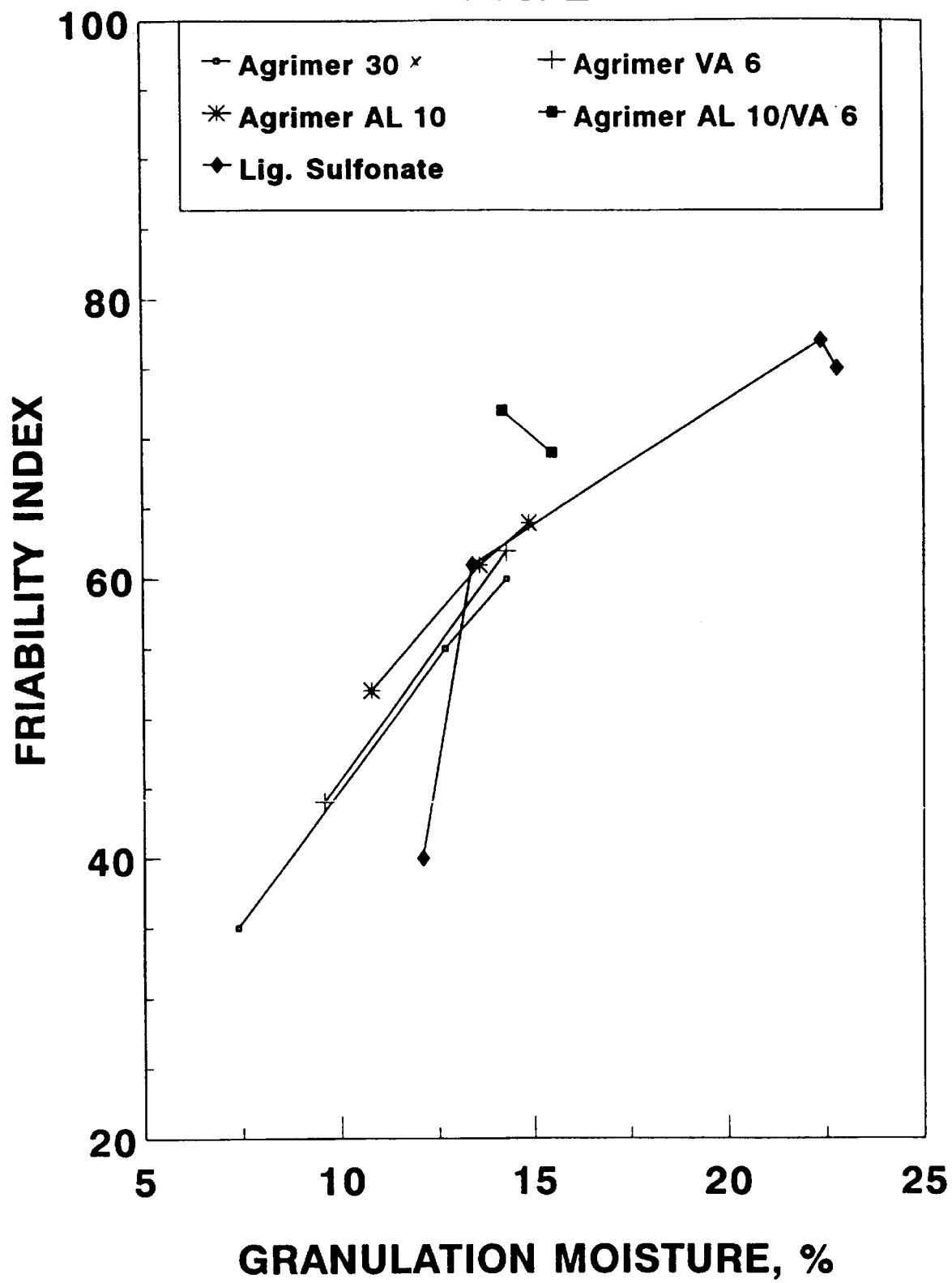

The data in FIGS. 1 and 2 show that water dispersible granules prepared with Agrimers® VA 6 and AL 10 as binders develop greater hardness and friability resistance at granulation moisture levels below 13% compared to granules prepared with ligninsulfonate. The reduced requirement for granulation moisture decreases energy consumption, and therefore, cost of drying granules. FIG. 2 also demonstrates that the mixture of Agrimers® VA 6 and AL 10 produce a synergistic increase in friability resistance of granules. Such granules will have a reduced tendency to fracture and form hazardous dusts.

The data in Table 2 show that water dispersible granules prepared with Agrimers® VA 6 and AL 10 as binders produce less sediment when suspended in water compared to granules prepared with ligninsulfonate. Improvement in dispersion leads to better efficiency in application of the pesticide. Table 2 also shows that Agrimer® AL 10 reduces foaming when used as the sole binder, or in combination with Agrimer® VA 6, compared to ligninsulfonate. Foam is undesirable in pesticide mix tanks because it retards mixing and reduces capacity.

The data in Table 3, summarizing the 1 kg scale experiments, is consistent with the other data. Granules with superior dispersion properties can be obtained with less moisture added, and with greater conversion efficiency leading to increased throughput.

TABLE 2

Suspension and Foam Test Results for Atrazine Water Dispersible Granules

| Binder | No. Expts. | Filtration Susp. % Susp. | Cone Disp. Sed. Index | Foam Index |
|---|---|---|---|---|
| 3% Ligninsulfonate | 4 | 86 | 5 | 57 |
| 3% Agrimer VA 6 | 3 | 86 | 1 | 61 |
| 3% Agrimer AL 10 | 4 | 87 | 2 | 26 |
| 1.5% Agrimer AL 10 + 1.5% Agrimer | 2 | 90 | 2.5 | 38 |

TABLE 3

Granule Conversion and Suspension Properties of 1 kg Batch Samples

| Binder | Granulation Moisture, % | Powder - Granule Conversion, % | Filtr. Susp % suspended | Cone Disp. sed. index |
|---|---|---|---|---|
| Ligninsulfonate | 15 | 60 | 78 | 13 |
| Agrimer ® VA 6 | 10 | 84 | 95 | 8.0 |
| Agrimer ® AL 10 | 8.0 | 88 | 85 | 6.7 |

What is claimed is:

1. A free-flowing, non-dusting water dispersible granule of an active agricultural chemical having low friability and effective crush strength for delivery to a desired site as a stable suspension in water, without deleterious foaming, comprising an active agricultural chemical and about 1–6% by weight thereof of a binder which will dissipate its bending action when the granule is immersed in water which is a copolymer of (a) vinylpyrrolidone and (b) a comonomer selected from butene and vinyl acetate, and mixtures thereof, and optional agents selected from the group consisting of defoamers, wetting agents and dispersing agents.

2. A water dispersible granule according to claim 1 wherein said binder is a graft copolymer of polyvinylpyrrolidone and butene.

3. A water dispersible granule according to claim 1 wherein said binder is a copolymer of vinylpyrrolidone and vinyl acetate.

4. A water dispersible granule according to claim 1 wherein said binder is a mixture of the graft copolymer of vinylpyrrolidone and butene, and a copolymer of vinylpyrrolidone vinyl acetate.

5. A water dispersible granule according to claim 4 wherein said binder is about a 1:1 mixture by weight of said graft copolymer and a copolymer of vinylpyrrolidone and vinyl acetate.

6. A water dispersible granule according to claim 1 wherein said binder is present in an amount of about 2–3% by weight of the granule.

7. A method of making the water dispersible granule of claim 1 which is prepared comprises granulating the components thereof with up to 25% water, and then drying to reduce the moisture content to about 1%.

* * * * *